United States Patent [19]

Lapidus

[11] 4,306,873

[45] Dec. 22, 1981

[54] AQUEOUS-BASED HAIR DYEING COMPOSITION CONTAINING A SOLUBLE BISMUTH SALT COMPLEX AND A REDUCING COMPOUND

[75] Inventor: Herbert Lapidus, Ridgefield, Conn.

[73] Assignee: Combe Incorporated, White Plains, N.Y.

[21] Appl. No.: 89,508

[22] Filed: Oct. 30, 1979

Related U.S. Application Data

[63] Continuation-in-part of Ser. No. 953,123, Oct. 20, 1978, abandoned.

[51] Int. Cl.$^3$ .......................... D06P 3/04; D06P 3/14
[52] U.S. Cl. ..................................... 8/405; 8/406; 8/416; 8/424; 8/426; 8/622
[58] Field of Search ................................. 8/622, 405

[56] References Cited

U.S. PATENT DOCUMENTS

| | | | |
|---|---|---|---|
| 1,937,365 | 11/1933 | Stoddard, Jr. et al. | 8/622 |
| 2,733,186 | 1/1956 | Brye | 8/424 |
| 2,763,269 | 9/1956 | Beste | 8/426 |
| 3,202,579 | 8/1956 | Berth et al. | 8/406 |
| 3,415,608 | 12/1968 | Tucker | 8/416 |
| 3,954,393 | 5/1976 | Lapidus | 8/405 |
| 4,195,972 | 4/1980 | Lapidus | 8/405 |

*Primary Examiner*—Dale R. Ore
*Attorney, Agent, or Firm*—Bryan & Bollo

[57] ABSTRACT

A hair dyeing composition comprising a water-soluble metal salt complex and a sulfur-containing reducing compound is described. In the composition, the metal salt complex is a water-insoluble bismuth salt of an alpha-hydroxy, polycarboxylic acid with a nitrogen-containing solubilizing agent.

13 Claims, No Drawings

AQUEOUS-BASED HAIR DYEING COMPOSITION CONTAINING A SOLUBLE BISMUTH SALT COMPLEX AND A REDUCING COMPOUND

BACKGROUND OF THE INVENTION

This invention pertains to a composition designed for use in dyeing human hair. While various forms of such dyeing compositions are known, a category of particular importance involves those containing a metal salt and a sulfur-containing reducing compound in an aqueous vehicle. Depending, in particular, upon the nature of the metal salt, these compositions may be employed to impart a variety of colors to human hair.

A class of metal salts which has proven particularly desirable is salts containing bismuth. Unfortunately, however, bismuth salts which are useful in such hair dyeing compositions have not proven readily susceptible to formulation.

This lack of success is formulating bismuth-containing hair dyeing compositions is partly a function of the limited number of known and active bismuth compounds which are soluble in conventional hair dyeing vehicles, particularly water. In addition, it is attributed to the low stability usually evidenced by bismuth salts in the presence of sulfur-containing reducing compounds. As a consequence, the use of bismuth salts for dyeing hair has been greatly limited.

In U.S. Pat. Nos. 1,937,365 and 2,719,104, there are described dyeing compositions utilizing inorganic salts of bismuth. These patents, however, require a number of different auxillary agents and indicated wide differences in coloration—viz. blond, red and brown—dependent upon these ingredients. Also, they are generally very unstable and so difficult to employ.

In U.S. Pat. No. 3,954,393, of Lapidus, there is disclosed another means by which useful hair dyeing compositions containing a bismuth salt may be obtained. There, an aqueous formulation including bismuth citrate solubilized by triethanolamine is described. That formulation yields various hair shades of brown. The scope of that invention is, however, limited. Consequently, many bismuth compounds remain unused.

DESCRIPTION OF THE INVENTION

The present invention is directed to the provision of a hair dyeing composition which, upon use, produces desirable color shades when applied to human hair. This composition contains a metal salt and sulfur-containing reducing compound in an aqueous vehicle. In this composition, the metal salt is a bismuth salt of an alpha-hydroxy, polycarboxylic acid rendered water-soluble with a nitrogen-containing complexing (or solubilizing) agent.

It has been discovered that the present water-soluble bismuth salt complexes are both active (in combination with a sulfur-containing reducing compound) to induce desirable coloring of hair and are natively water-soluble. Moreover, these complexes are quite stable in the presence of sulfur-containing reducing compounds until applied to the hair. As a consequence, a hair dyeing composition which is simply and readily prepared may be formulated.

In the present compositions, the anion of the present bismuth salts is obtained from alpha-hydroxy, polycarboxylic acids—especially alpha-hydroxy, dicarboxylic acids. Exemplary of such acids are malic and tartaric acid. The composition of the present acids may vary greatly, so long as they maintain at least an alpha-hydroxy, dicarboxylic moiety. In general, however, the acids contain between 3 and 20, preferably 3 to 10, and most preferably 3 to 5, carbons. Thus, they include saccharic acid, mucic acid, and the tri-hydroxy, glutaric acids. These bismuth salts are natively insoluble in water and most conventional hair dyeing vehicles.

Other than the alpha-hydroxy, di- or other polycarboxylic moiety, it is also generally preferred that the remainder of the acid be composed essentially of a hydrocarbon, normally a saturated hydrocarbon such as an alkyl group. Alternatively preferred are the alcohol derivatives of these hydrocarbons such as a hydroxy substituted alkyl group, so as to result in a poly-hydroxylated acid. In addition to the foregoing, however, various substituents, including halide, keto, aldehydic and other functional groups may be present.

The amount of bismuth salt employed in the present compositions may vary generally within conventional limits. Customarily, however, this salt is present in an amount of up to about 5%, preferably 0.1 to 1.0% and most preferably 0.25 to 0.75% by total weight of the composition. This degree of dilution permits ready control over the extent of hair dyeing.

These bismuth salts are solubilized by addition of a nitrogen-containing complexing agent. Exemplary agents include ammonia and triethanolamine (which is particularly preferred because of its low skin irritability); however, others are readily identified. Sufficient complexing agent, normally at least 50 and preferably between about 100 and 400 mole per mole of bismuth, should be employed to ensure the solubility of the resultant complex in the hair dyeing composition.

To produce a hair dyeing composition in accordance with the present invention, the bismuth salt of an alpha-hydroxy, polycarboxylic acid may initially simply be dissolved in all, or a portion, of the aqueous hair dyeing vehicle containing the complexing agent. Alternatively, this complex may be produced in situ by reaction of a different bismuth salt (normally a water-insoluble bismuth salt, such as bismuth nitrate or bismuth subnitrate) with a suitable alpha-hydroxy, polycarboxylic acid (usually an excess thereof, ranging between about 1 and 4 mole per mole of bismuth) in the presence of the complexing agent.

The sulfur-containing reducing compound utilized in accordance with the present invention may be selected from among any of the conventional agents for hair dyeing compositions. Exemplary are thiourea and thioglycolates. In a preferred embodiment in accordance with the present invention, however, the reducing compound is either sulfur or thiosulfate (normally the ammonium or alkali metal salts thereof.) Sulfur is generally employed in its finely divided, suspendable form. Thiosulfates, on the other hand, are water-soluble and hence readily employed in dissolved form in the present compositions.

The reducing compound of the present invention may be utilized in any effective amount as, for example, known for other metallic salt dyes or as is readily determined. These compounds are, however, customarily employed in a mole ratio of from about 0.5:1 to 10:1, most preferably 1:1 to 3:1 based upon the bismuth present.

The vehicle for the present dye system of a bismuth salt complex and a reducing compound comprises water and normally is at least 30%, preferably between 60 and 100% water by total weight. The remaining non-aqueous portion, if any, of the vehicle may be any liquid miscible therewith.

The amount of vehicle (or aqueous solvent) of the present invention will vary in conventional manner. It is preferred, however, that such vehicle constitute between about 50 and 90%, most preferably 75 and 90% by total composition weight. This ensures a manageable dyeing strength for the present compositions.

In preparing the hair dyeing compositions of the present invention, it is generally most convenient first to prepare separate aqueous portions of the soluble bismuth complex and of the reducing compound. These two portions may then be mixed together to produce the present composition. The resultant composition remains quite stable, without any substantial undesirable precipitation. When applied to the hair, it appears that a form of the chemical reaction influenced by the keratinaceous nature of hair and/or various other hair components such as oil, takes place. This reaction is manifested, in part, by the darkening or dyeing of the hair to the desired shade.

Of major importance to the present invention is the foregoing fact that it is only upon contact with the hair that substantial reaction between the bismuth complex and the reducing compound is commenced. Therefore, the compositions remain stable until activated by the hair they are intended to dye.

While a soluble complex of a bismuth salt of an alpha-hydroxy, polycarboxylic acid with a nitrogen-containing complexing agent, a reducing component and an aqueous vehicle are the essential components of the composition of this invention, it is understood that various additional ingredients may be present. These include, for example, such conventional additives as a wetting agent which will facilitate the dispersion of, for example, sulfur. Particularly preferred as a wetting agent are ethylene oxide-alcohol condensation products such as Triton X-100 (a Rohm & Haas condensation product of iso octyl phenyl polyethoxy ethanol with between 9 and 10 moles of ethylene oxide). Similarly, a humectant such as glycerin may be employed to stabilize the reaction on the hair. Grooming agents, such as propylene glycol, mineral oil, fatty acid esters and the like, may also be present. Where water immiscible, these agents are normally emulsified with the aqueous dye system to produce a lotion form of product. Further, perfumes and the like may be incorporated into the composition.

The hair dyeing compositions of this invention normally exhibit a pH of between 7.5 and 10.5, preferably 8.0 and 10.0. These have been found to ensure stability of the composition while permitting application to the hair without adverse affect.

In addition to the foregoing conventional additives for hair dyeing composition, a particularly preferred additive is N-acetyl ethanolamine (often referred to as Acetamide MEA). This compound, particularly in an amount of from about 1 to 25%, most preferably 10 to 15% by total weight of composition has been discovered to be a highly desirable dyeing enhancer. Its use in dye systems in general is described in detail in United States continuation-in-part application Ser. No. 37,547 of Herbert Lapidus, entitled DYEING COMPOSITION FOR FIBROUS MATERIALS, filed on May 11, 1979, the disclosure of which is incorporated herein by reference. N-acetyl ethanolamine will greatly accelerate and deepen the coloring effect of the present composition. In addition, it has been found to render the resultant color more resistant to fading or removal from the hair.

In order to more clearly describe the invention, several examples of compositions of the present invention are described below. It should be understood, however, that these examples are provided solely for illustration and are not intended to limit the scope of the invention.

EXAMPLE I

| Ingredients | Percent (by total weight) |
|---|---|
| Bismuth sub nitrate | 0.30% |
| Malic Acid | 3.00% |
| Glycerin | 10.00% |
| Aqueous ammonia (28%) | 5.00% |
| Sulfur (precipitated) | 1.00% |
| Triton X-100 | 0.10% |
| Water | 80.60% |

A hair dyeing composition having the above-indicated formula was prepared as follows:
(a) The sulfur and Triton X-100 were added to an aliquot of water and ground to disperse the sulfur in fine, semi-colloidal form;
(b) The bismuth sub nitrate, glycerin, malic acid, ammonia, and 10% of the water were placed in a kettle and heated at 70° C. until clear. During heating, the malic acid displaced the nitrate to form bismuth malate, which complexed with the ammonia;
(c) The solution resultant from Step (b) was mixed with the remaining water and then the solution of Step (a) to produce the composition.

To test the above composition, swatches of bleached hair were dunked into the hair dyeing composition, removed, shaken to remove excess composition, and then permitted to dry overnight at room temperature. After drying, the hair was observed to have changed from its initial blondish color to a shade of brown. Repeated daily treatments over three weeks yielded an increasing deeper or darkened shade of brown.

EXAMPLE II

| Ingredients | Percent (by total weight) |
|---|---|
| Bismuth sub nitrate | 0.25% |
| Tartaric Acid | 2.00% |
| Triethanolamine | 3.00% |
| Glycerin | 10.00% |
| Sulfur (precipitated) | 1.00% |
| Triton X-100 | 0.10% |
| Water | 83.65% |

A hair dyeing composition having the above-indicated ingredients were prepared, using the procedure set forth in Example I. This composition again evidenced the ability to dye bleached hair to a dark shade of brown.

It should be understood by those skilled in the art that various modifications may be made in the present invention without departing from the spirit and scope thereof as described in the specification and defined in the appended claims.

What is claimed is:
1. In a hair dyeing composition comprising a metal salt and a sulfur-containing reducing compound in an aqueous vehicle, the improvement wherein said metal salt comprises a water-soluble complex of a bismuth salt of an alpha-hydroxy, polycarboxylic acid amounting up to about 5% by total weight of the composition, with a nitrogen-containing complexing agent selected from the group consisting of ammonia and triethanolamine amounting to from 50 to about 400 moles per mole of bismuth, said reducing compound amounting to from about 0.5 to 10 moles per mole of bismuth.

2. The composition of claim 1, wherein the alpha-hydroxy, polycarboxylic acid is malic acid.

3. The composition of claim 1, wherein the alpha-hydroxy, polycarboxylic acid is tartaric acid.

4. The composition of claim 1, wherein the reducing compound is sulfur.

5. The composition of claim 1, wherein the reducing compound is an alkali metal thiosulfate.

6. The composition of claim 1, wherein the anion of the bismuth salt is a poly-hydroxy, polycarboxylic acid.

7. The composition of claim 1, wherein the anion of the bismuth salt is an acid having between 3 and 20 carbons.

8. The composition of claim 1, wherein the complexing agent is ammonia.

9. The composition of claim 1, wherein the complexing agent is triethanolamine.

10. The composition of claim 1, wherein the composition additionally contains N-acetyl ethanolamine.

11. The composition of claim 1, wherein the pH of the composition is between about 7.5 and 10.5.

12. The composition of claim 1, wherein the anion of the bismuth salt is an alpha-hydroxy, di-carboxylic acid.

13. The composition of claim 1, wherein the anion of the bismuth salt is a poly-hydroxy, di-carboxylic acid.

* * * * *